(12) United States Patent
Kraemer et al.

(10) Patent No.: US 6,395,231 B1
(45) Date of Patent: May 28, 2002

(54) PIPETTE AND HANDLING AUTOMATIC MACHINE FOR MICROTITRATION PLATES WITH PERMEABLE BASES

(75) Inventors: Wolfgang Kraemer; Uwe Naumann, both of Jena; Thomas Moore, Jena-Drackendorf, all of (DE)

(73) Assignee: CyBio Instruments GmbH, Jena (DE)

( * ) Notice: Subject to any disclaimer, the term of this patent is extended or adjusted under 35 U.S.C. 154(b) by 0 days.

(21) Appl. No.: 09/331,221

(22) PCT Filed: Sep. 24, 1998

(86) PCT No.: PCT/EP98/06089

§ 371 (c)(1),
(2), (4) Date: Aug. 20, 1999

(87) PCT Pub. No.: WO99/21016

PCT Pub. Date: Apr. 29, 1999

(30) Foreign Application Priority Data

Oct. 21, 1997 (DE) .......................... 197 46 455

(51) Int. Cl.[7] .............................. B01L 3/02; B01L 11/00; B32B 27/04

(52) U.S. Cl. .................. 422/100; 422/101; 422/65; 141/7; 141/130; 141/135

(58) Field of Search ................ 422/100, 101, 422/65, 67, 68.1; 73/864.91, 864, 864.01; 141/65, 7, 130, 135; 222/152

(56) References Cited

U.S. PATENT DOCUMENTS

| | | | | |
|---|---|---|---|---|
| 3,650,306 A | * | 3/1972 | Lancaster | 141/238 |
| 4,151,931 A | * | 5/1979 | Scherer et al. | 221/226 |
| 4,427,415 A | * | 1/1984 | Cleveland | 436/57 |
| 4,461,328 A | * | 7/1984 | Kenny | 141/67 |
| 4,772,487 A | | 9/1988 | Gotoh et al. | |
| 4,948,442 A | * | 8/1990 | Manns | 156/73.1 |
| 5,047,215 A | * | 9/1991 | Manns | 422/101 |
| 5,055,408 A | * | 10/1991 | Higo et al. | 436/48 |
| 5,201,348 A | | 4/1993 | Werner | |
| 5,266,272 A | * | 11/1993 | Griner et al. | 422/104 |
| 5,273,718 A | | 12/1993 | Andersson et al. | |

(List continued on next page.)

FOREIGN PATENT DOCUMENTS

| | | |
|---|---|---|
| EP | 0 351 988 | 1/1990 |
| EP | 0 829 291 | 3/1998 |
| WO | WO 87 06008 | 10/1987 |

OTHER PUBLICATIONS

English Abstract of DE 33 46 532.
English Abstract of DE 34 90 484.
English Abstract of DE 38 05 808.
English Abstract of DE 38 41 961.
English Abstract of DE 41 07 262.
Robbins Sciebtific, Hydra 96 (May) Article: 96 Channel Microdispenser for Microchemistry & Micro Cell Culture Applications (5 pgs).

*Primary Examiner*—Jill Warden
*Assistant Examiner*—Brian R. Gordon
(74) *Attorney, Agent, or Firm*—Reed Smith LLP

(57) ABSTRACT

A device for filling and suction of filter plates in a microtitration plate format which is comprised of a simultaneously working multipipette, two stacking elements, a plate transfer car with a suction station, four lifting drives, and an electric plate holder. The plates emanating from the dispensing stacking elements are filled by the pipettes or the pipette automatic machine and can be deposited on the suction station afterwards with the aid of the plate holder and the lifter. The plates are then lifted together with the weight such that the plate is sufficiently pressed hard on the seal in the suction station. As a result, a corresponding low pressure can be generated in the vacuum station.

6 Claims, 4 Drawing Sheets

U.S. PATENT DOCUMENTS

| | | | |
|---|---|---|---|
| 5,306,420 A | * | 4/1994 | Bisconte ..................... 210/143 |
| 5,324,480 A | * | 6/1994 | Shumate et al. ............... 422/63 |
| 5,348,606 A | * | 9/1994 | Hanaway et al. ............ 156/292 |
| 5,415,060 A | * | 5/1995 | DeStefano, Jr. .............. 74/540 |
| 5,487,872 A | * | 1/1996 | Hafeman et al. ........... 422/102 |
| 5,620,894 A | | 4/1997 | Barger et al. |
| 5,645,723 A | | 7/1997 | Fujishiro et al. |
| 5,824,224 A | * | 10/1998 | Fujishiro et al. ............ 210/651 |
| 5,928,952 A | * | 7/1999 | Hutchins et al. ............... 436/50 |
| 5,939,024 A | * | 8/1999 | Robertson ................... 422/101 |
| 6,039,211 A | * | 3/2000 | Slater et al. .................... 222/1 |
| 6,106,783 A | * | 8/2000 | Gamble ....................... 422/102 |
| 6,148,878 A | * | 11/2000 | Ganz et al. ................. 141/129 |
| 6,182,719 B1 | * | 2/2001 | Yahiro ........................ 141/130 |

* cited by examiner

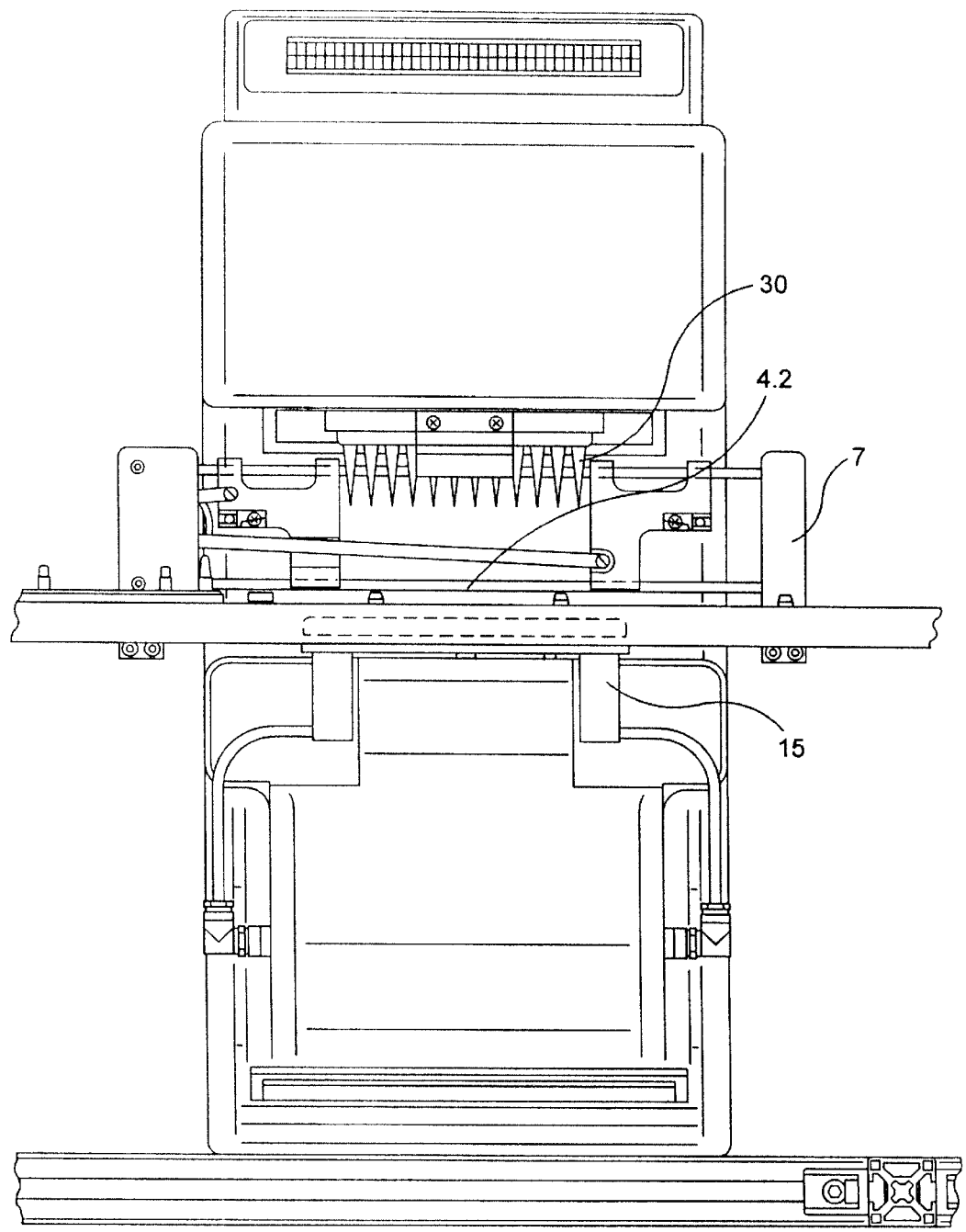
F I G. 3

PIPETTE AND HANDLING AUTOMATIC MACHINE FOR MICROTITRATION PLATES WITH PERMEABLE BASES

BACKGROUND OF THE INVENTION

1. Field of the Invention

The invention relates to an automatic pipetting and handling machine for microtitration plates with a, permeable base, e.g. filter of plates or membrain bottom plates.

2. Description of the Prior Art

Microtitration plates with permeable bases have been in use in screening laboratories for a number of years. There is a wide range of products, which differ with regard to the type of bases and therefore with regard to their interaction with the liquid media situated in the so-called wells. The handling of liquid using these filter plates can essentially be described by means of the following steps: filling the wells with liquid from above and, after a reaction time, sucking the liquid downward through the filter layer. The filling step is carried out using conventional handheld pipettes or pipetting robots and does not differ from the procedure used for conventional microtitration plates. The suction step, or emptying of the wells, is not carried out via the openings of the latter, but rather, at so-called suction stations, through the base of the wells. The structure of these suction stations is essentially as follows. The filter plate is placed onto a suction tray, which has a surrounding rubber seal in the area where the edge of the filter plate rests. On the bottom of the suction tray, there is an opening which is connected to a vacuum device. This vacuum device generally comprises a Woulff bottle for separating off the liquid, an aeration valve and a vacuum pump. When working manually, the procedure is as follows. The filled filter plate is placed and pressed onto the suction tray, and at the same time a vacuum is applied to the suction tray via its opening. An important factor here, depending on the design of the filter plate, is whether the vacuum is built up slowly by a pump being switched on or is brought about suddenly by connecting the vacuum with a nominal pressure.

The automatic procedure is similar to the manual sequence, in that either the filter plate is filled by a pipetting robot directly at the suction station, or, if the pipetting robot has a plate-gripping mechanism, it pipettes the plates and then deposits them on the suction device for the suction period. In the latter case, it is possible for the gripper arm to press the filter plate onto the suction station, in order to enable it to be sucked on securely so that the vacuum can be built up. Naturally, the forces which can be applied to do this are low. In the first of the two cases, it is still possible to apply the filter plate with a vacuum shock.

The throughput of such appliances is limited by the number of needles available for liquid handling; known systems are fitted with one to eight needles.

Furthermore, systems with an integrated gripper are relatively large and slow. The size of such an appliance is important, since it is often necessary to carry out the process described above in a workbench which is protected by means of a laminar air flow.

OBJECT AND SUMMARY OF THE INVENTION

The invention is based object of providing a compact arrangement with which filter plates can be removed from a storage system, pipetted, sucked empty and stored automatically, in an efficient time and with a high throughput.

According to the invention, this object is achieved by an automatic pipetting and handling machine for microtitration plates with a permeable base, comprising a carriage which can be displaced on a horizontal guide path. The carriage has a dispenser stacking section, a storage stacking section, an automatic pipetting machine and a pressure station arranged along the guide path. The carriage also has a suction station.

BRIEF DESCRIPTION OF THE DRAWINGS

The invention is to be explained in more detail below with reference to drawings, in which:

FIG. 3 shows a basic structure of an automatic pipetting machine

DESCRIPTION OF THE PREFERRED EMBODIMENTS

Figure 1:
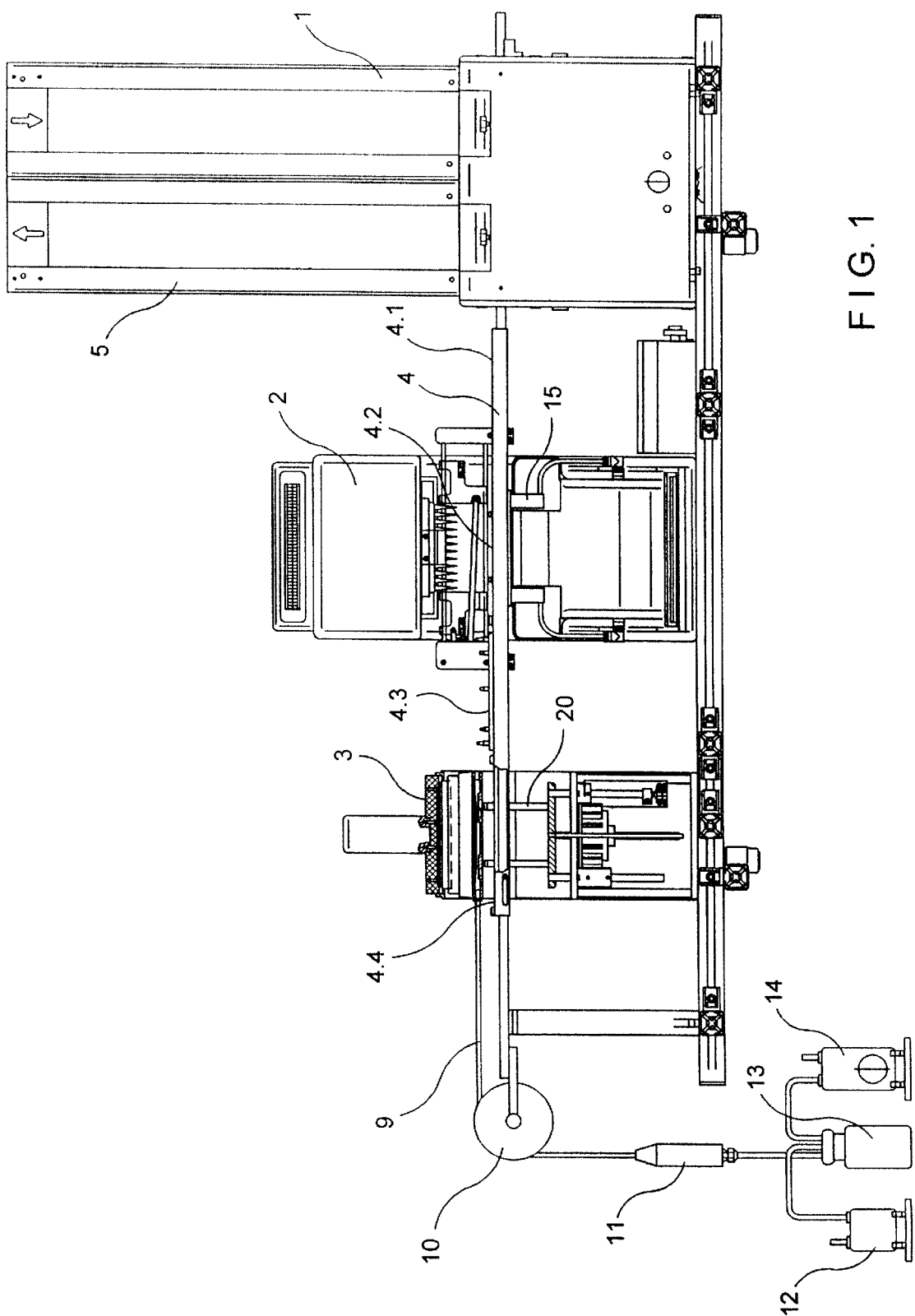
FIG. 1 shows a basic structure of an automatic pipetting and handling machine according to the invention
Figure 2:
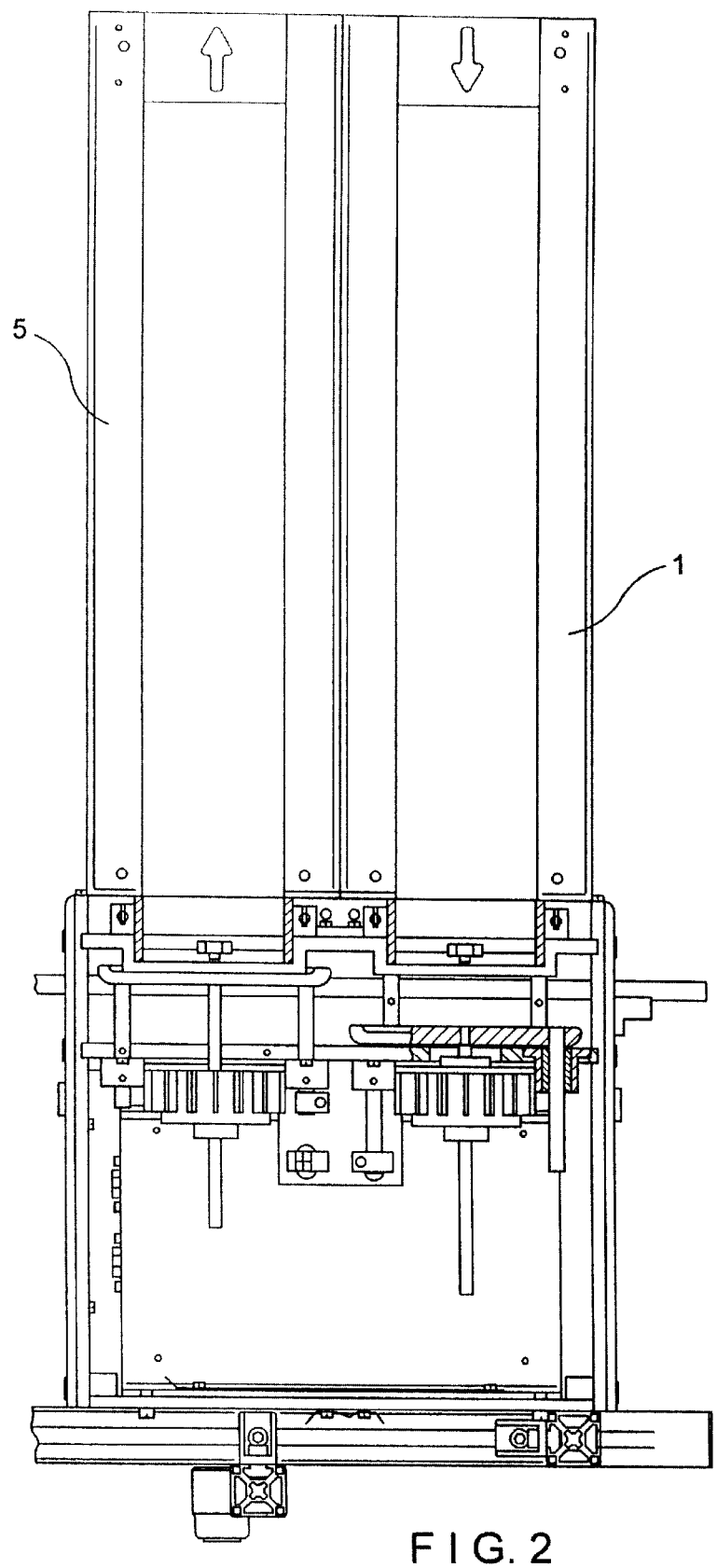
FIG. 2 shows a basic structure of a dispensing and storage stacking section.

In accordance with FIG. 1, the automatic pipetting and handling machine comprises a dispensing stacking section 1, an automatic pipetting machine 2, a pressure station 3, a carriage 4 and a storage stacking section 5. As can be seen from FIG. 1, the carriage 4 is guided horizontally along a system of rails and thus, in its working steps, which can be subdivided as follows:

a) starting position, i.e. with its right-hand support surface in the dispensing stacking section 1 in order to receive the filter plate b) first intermediate position, i.e. with its right-hand support surface in the automatic pipetting machine 2 c) second intermediate position, i.e. with its left-hand support surface in the automatic pipetting machine 2 d) third intermediate position, i.e. with its left-hand support surface in the pressure station 3 e) fourth intermediate position, i.e. with its left-hand support surface in the automatic pipetting machine 2 f) fifth intermediate position, i.e. with its right-hand support surface in the automatic pipetting machine 2 g) end position, i.e. with its right-hand support surface in the storage stacking section 5 in order to deliver the filter plate produces the connection between the dispensing stacking section 1, automatic pipetting machine 2, pressure station 3 and storage stacking section 5. In this embodiment, the carriage 4 has four support surfaces (4.1, 4.2, 4.3, 4.4) which lie next to one another, the outermost right-hand support surface 4.1 being reserved to receive the filter plates, the outermost left-hand support surface 4.4 being covered with a suction station 6, while one of the intermediate support surfaces 4.2 is covered with a vessel 30 and the other 4.3 is covered with a rinsing tray 40. The middle support surfaces (4.2, 4.3) could be dispensed with if, for example, one were to use a pipetting device which is able to fill its pipettes from behind via a separate vessel and changes its tips after each pipetting operation, so that the rinsing part can be omitted.

Figure 4:
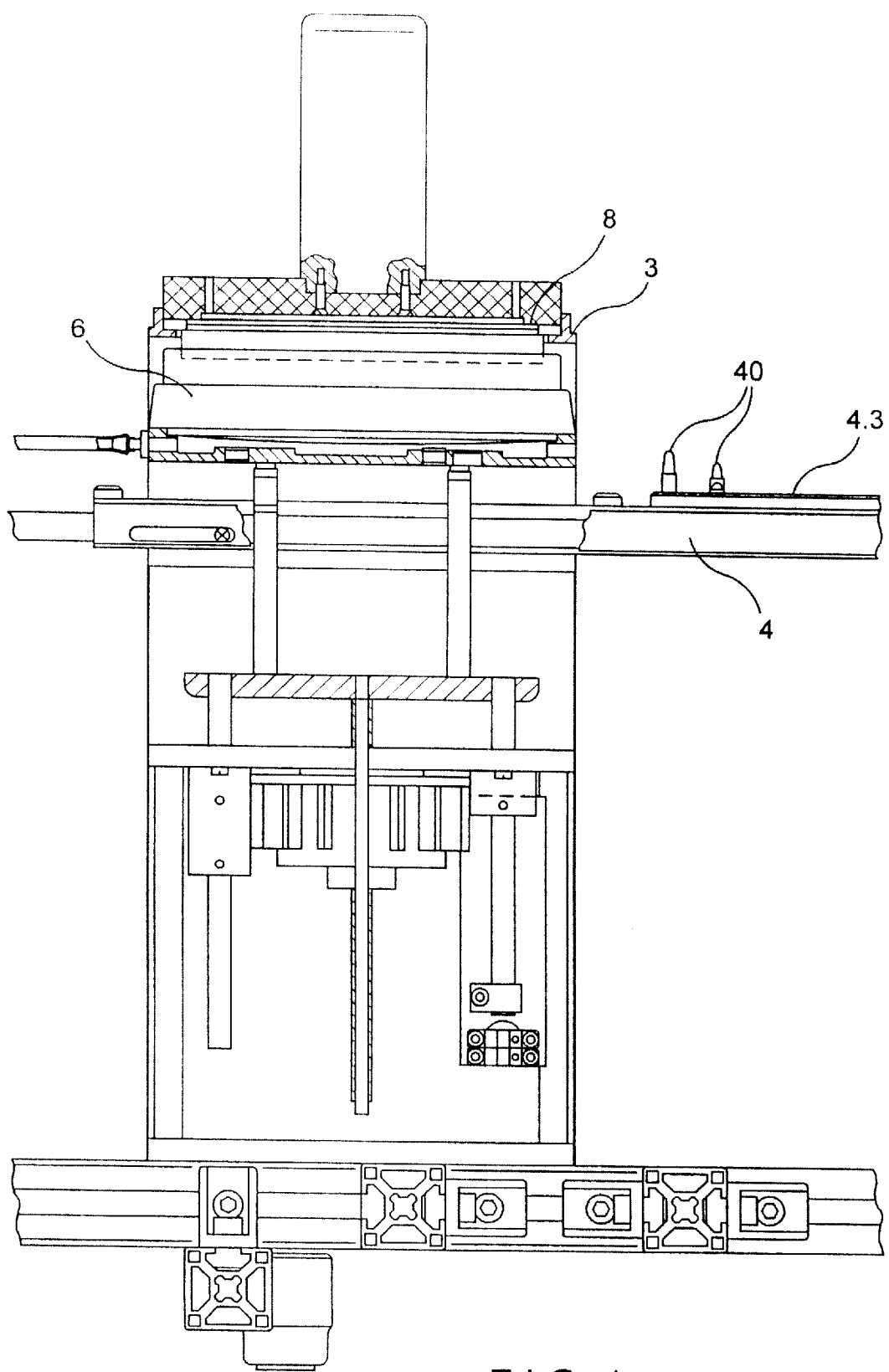
FIG. 4 shows a basic structure of a pressure station.

The dispensing stacking section 1, in which the filter plates are stacked, is provided for the purpose of holding a stock of filter plates. A second, storage stacking section 5, which is an identically designed stacking section arranged directly next to the dispensing stacking station 1, in accordance with FIG. 1, is used to store the finished filter plates. These stacking sections, with the aid of a lifter assigned to each of them and of a catch mechanism, are able either to deposit a filter plate on a carriage or to receive a filter plate from the carriage. The catches are controlled electromagnetically as a function of the lifter height. In the starting position of the carriage 4, the latter is covered with a filter plate on its right-hand outermost support surface by means of the lifter. Then, the carriage 4 moves into the first intermediate position, and the lifter 15 of the automatic pipetting machine 2 lifts the filter plate horizontally up to the pipettes, so that the appropriate wells can be filled. After the filling operation, the lifter 15 lowers the filled filter plate and transfers it to a plate holder 7, as can be seen from FIG. 3. The lifter is lowered further into its lower end position. Then, the carriage 4 moves into its second intermediate position, and the lifter of the automatic pipetting machine 2 lifts the suction station 6 up to the filter plate. The plate holder 7 releases the filter plate again, and the lifter moves downward into its starting position, thus placing the suction station 6, with the filter plate above it, onto the carriage 4. The carriage then moves to the third intermediate position, into the pressure station 3. The pressure station 3, in accordance with FIG. 4, comprises a lifter 20, which is situated beneath the guide path of the carriage 4, and a bearing surface 8, which is situated a distance above the lifter 20, so that the carriage 4, which is laden with the suction station 6 and the filter plate above it, can move or be guided beneath the bearing surface. The lifter 20 of the pressure station 3 lifts and presses the suction station, with the filter plate attached, against the bearing surface, so that a sealing action between filter plate and suction station 6 is achieved before the vacuum is applied. The bearing surface exerts, from above, an oppositely directed force to that of the lifter on the filter plate and, as can be seen from FIG. 4, may comprise a mounted weight. It is conceivable to use an embodiment which is not illustrated and in which the lifter presses onto the filter plate from above, thus producing the necessary sealing action. The necessary vacuum is produced, in accordance with FIG. 1, by means of the essential units comprising suction hose 9, hose-guidance roll 10, hose weight 11, aeration valve 12, Woulff bottle 13 and vacuum pump 14, by starting the vacuum pump 14. After a suitable suction period, air is introduced into the suction tray via the aeration valve 12. After the suction operation has finished, the lifter of the pressure station 3 moves back into its starting position, thus placing the suction station 6, together with the emptied filter plate, onto the carriage 4, so that the latter adopts the fourth intermediate position. The lifter of the automatic pipetting machine 2 lifts the suction station 6, together with the filter plate located above it, up to the plate holder 7, which holds the filter plate; the lifter is then lowered into its starting position, thus placing the suction station 6 onto the carriage 4. The carriage 4 adopts the fifth intermediate position, the lifter is guided to the filter plate, the plate holder 7 releases the filter plate again, and the lifter adopts its starting position, placing the filter plate onto the carriage 4. Then, the carriage 4 proceeds to its end position, so that it is located in the storage stacking section 5. The lifter of the storage stacking section 5 takes hold of the filter plate and places it in the storage stacking section 5.

While the foregoing description and drawings represent the present invention, it will be obvious to those skilled in the art that various changes may be made therein without departing from the true spirit and scope of the present invention.

What is claimed is:

1. An automatic pipetting and handling machine for microtitration plates with a permeable base, comprising:

a carriage which can be displaced on a horizontal guide path;

a dispenser stacking section, a storage stacking section arranged along the guide path, an automatic pipetting machine arranged along the guide path, and a pressure station arranged along the guide path; and said carriage having a suction station wherein the suction station is connected to a system which generates a vacuum;

wherein the system which generates a vacuum comprises a suction hose connected to the suction station, a hose-guidance roll, a hose weight, an aeration valve, a Woulff bottle and a vacuum pump connected to the Woulff bottle.

2. The automatic pipetting and handling machine according to claim 1, wherein the pressure station comprises a lifter, which is situated beneath the guide path of the carriage, and a bearing surface, which is situated a distance above the lifter, so that the carriage, which is laden with the suction station and a filter plate above it, can move beneath the bearing surface.

3. The automatic pipetting and handling machine according to claim 2, wherein the bearing surface is designed as a mounted weight.

4. The automatic pipetting and handling machine according to claim 2, wherein the bearing surface is designed as a horizontally fixed bearing surface.

5. The automatic pipetting and handling machine according to claim 1, wherein the carriage has four support surfaces arranged next to one another, one outer support surface being covered with the suction station, which can be lifted off, and the other outer support surface being reserved to accommodate the filter plates, while one of the intermediate support surfaces is provided for a liquid reservoir vessel and the other is provided for a washing station.

6. The automatic pipetting and handling machine according to claim 1, wherein the carriage has a left-hand and a right-hand support surface, one of which is covered with the suction station and the other of which is intended to accommodate the filter plates.

* * * * *